(12) United States Patent
Wessman

(10) Patent No.: US 6,409,708 B1
(45) Date of Patent: *Jun. 25, 2002

(54) APPARATUS FOR ADMINISTRATING TOXIC FLUID

(75) Inventor: Göran Wessman, Göteborg (SE)

(73) Assignee: Carmel Pharma AB, Gothenburg (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/304,695

(22) Filed: May 4, 1999

Related U.S. Application Data

(63) Continuation of application No. PCT/SE96/01411, filed on Nov. 4, 1996.

(51) Int. Cl.$^7$ ............................................. A61M 25/00
(52) U.S. Cl. ........................ 604/284; 604/411; 604/414
(58) Field of Search ................................. 604/284, 256, 604/282, 283, 45, 412, 413, 414, 164.02, 164.04, 164.07, 164.06, 164.1, 164.11, 167.01, 167.02, 167.03, 167.06, 173, 246, 201, 205, 264, 905, 8, 39, 506; 138/110

(56) References Cited

U.S. PATENT DOCUMENTS

| 4,256,106 A | 3/1981 | Shoor ........................ 128/247 |
| 4,334,551 A | 6/1982 | Pfister ................... 137/614.03 |

(List continued on next page.)

FOREIGN PATENT DOCUMENTS

| DE | 2206908 | 2/1972 |
| SE | 434700 | 8/1984 |
| SE | 8800337 | 2/1988 |

*Primary Examiner*—Brian L. Casler
*Assistant Examiner*—Kevin C. Sirmons
(74) *Attorney, Agent, or Firm*—Norris, McLaughlin & Marcus

(57) ABSTRACT

Device for administrating a toxic fluid, comprising an infusion device for connection to an infusion bag. The infusion device is provided with an insertion portion for connecting the bag, and an infusion chamber for dosing a fluid flow via a flow duct in the insertion portion from the bag to an outlet arranged on the chamber. The insertion portion also comprises a ventilating duct which extends between the bag and the outside of the infusion device and ends in a connection arranged on the side of the infusion device for supplying fluid to be administrated. The connection is provided with at least one membrane which is air tight and penetrable by an injection needle.

2 Claims, 2 Drawing Sheets

U.S. PATENT DOCUMENTS

| | | | |
|---|---|---|---|
| 4,458,733 A | | 7/1984 | Lyons .......................... 141/1 |
| 4,610,683 A | * | 9/1986 | Vaillancourt ................ 604/405 |
| 4,743,243 A | * | 5/1988 | Vaillancourt ................ 604/405 |
| 4,758,225 A | * | 7/1988 | Cox et al. ................... 604/126 |
| 4,787,898 A | | 11/1988 | Raines ........................ 604/411 |
| 4,857,068 A | * | 8/1989 | Kahn .......................... 604/126 |
| 4,865,583 A | * | 9/1989 | Tu .............................. 604/248 |
| 4,874,377 A | * | 10/1989 | Newgard et al. ........... 604/167 |
| 4,935,010 A | * | 6/1990 | Cox et al. ................... 604/122 |
| 4,998,926 A | * | 3/1991 | Alchas ........................ 604/251 |
| 5,006,114 A | * | 4/1991 | Rogers et al. .............. 604/167 |
| 5,053,014 A | * | 10/1991 | Heugten ..................... 604/167 |
| 5,084,023 A | * | 1/1992 | Lemieux |
| 5,098,407 A | * | 3/1992 | Okamura .................... 604/248 |
| 5,176,653 A | * | 1/1993 | Metals .................... 604/167.02 |
| 5,364,369 A | * | 11/1994 | Reynolds .................... 604/187 |
| 5,456,675 A | * | 10/1995 | Wolbring et al. ........... 604/280 |
| 5,466,230 A | * | 11/1995 | Davila ........................ 604/256 |
| 5,599,346 A | * | 2/1997 | Edwards et al. .............. 606/41 |
| 5,636,660 A | * | 6/1997 | Pfleiderer et al. ........... 137/550 |
| 5,643,227 A | * | 7/1997 | Stevens ...................... 604/264 |
| 5,695,479 A | * | 12/1997 | Jagpal ........................ 604/264 |
| 5,743,891 A | * | 4/1998 | Tolkoff et al. .............. 604/282 |
| 5,782,817 A | * | 7/1998 | Franzel et al. .............. 604/256 |
| 5,800,384 A | * | 9/1998 | Russell et al. ......... 604/164.01 |
| 5,807,350 A | * | 9/1998 | Diaz .......................... 604/256 |
| 5,839,715 A | * | 11/1998 | Leinsing .................. 251/149.1 |
| 5,916,193 A | * | 6/1999 | Stevens et al. ................ 604/53 |
| 5,984,902 A | * | 11/1999 | Moorehead ................ 604/247 |
| 5,997,515 A | * | 12/1999 | de la Torre et al. ........ 604/256 |
| 6,024,729 A | * | 2/2000 | Dehdashtian et al. ....... 604/256 |
| 6,042,567 A | * | 3/2000 | McNamara ................. 604/168 |
| 6,139,534 A | * | 10/2000 | Niedospial et al. ......... 604/403 |
| 6,261,267 B1 | * | 7/2001 | Chen .......................... 604/247 |

\* cited by examiner

APPARATUS FOR ADMINISTRATING TOXIC FLUID

This application is a continuation of PCT/SE96/01411 filed Nov. 4, 1996.

BACKGROUND OF THE INVENTION

1. Field of the Invention

The present invention relates to a device for administrating a toxic fluid, comprising an infusion device for connection to an infusion bag, which infusion device is provided with an insertion portion for connecting the bag, and an infusion chamber for dosing a fluid flow via a flow duct in the insertion portion from the bag to an outlet arranged on the chamber, which insertion portion also comprises a ventilating duct which extends between the bag and the outside of the infusion device and ends in a connection arranged on the side of the infusion device for supplying the fluid to be administrated.

In medical care highly toxic fluids, e.g. cytotoxic drugs or antiviral antibiotics, are dealt with. Each discharge of such fluids entails health hazards for staff and patients. Protective equipment should always be used when handling such fluids, e.g. fume cupboards, protective gloves and garments.

2. Description of the Related Art

A system with penetrable double membranes is disclosed in SE-B-434,700, which system facilitates preparation and administration of a toxic fluid without it coming into contact with breathable air. However, there are still drawbacks when administrating to a patient via infusion, whereby an injector connected to the conical connection of an infusion bag of standard type under certain circumstances could come loose. In such a case are both membranes penetrated, so that discharge to breathable air can take place.

SUMMARY OF THE INVENTION

The purpose of the present invention is to accomplish an injector connection for supplying drugs to an infusion bag of standard type, which connection eliminates the risk of the drug coming in contact with breathable air.

This is accomplished according to the invention by the connection being provided with at least one membrane, which is air tight and penetrable by an injection needle.

DESCRIPTION OF A PREFERRED EMBODIMENT

Figure 1:
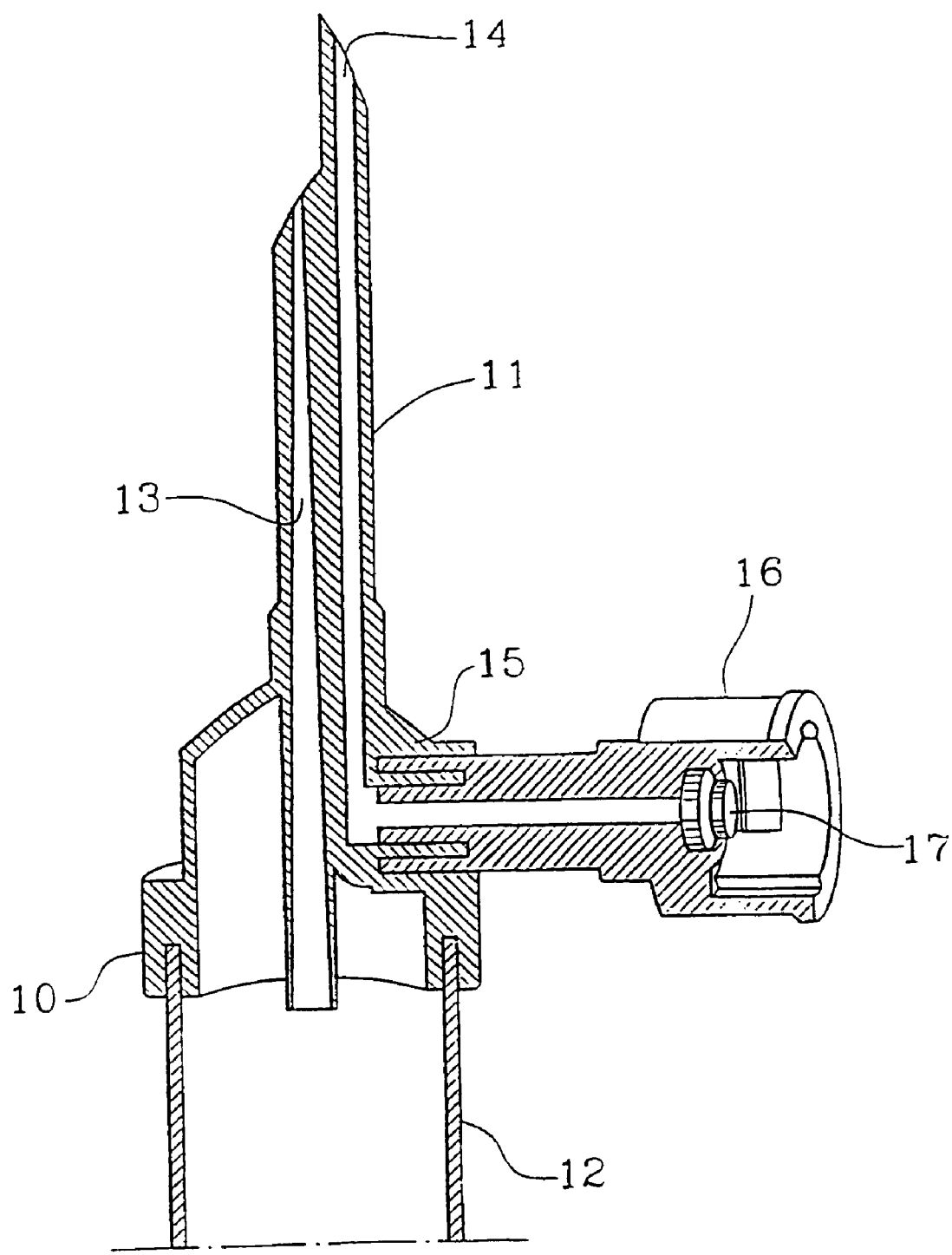
FIG. 1 is a partial cross-sectional view of the infusion device of the invention.
Figure 2:
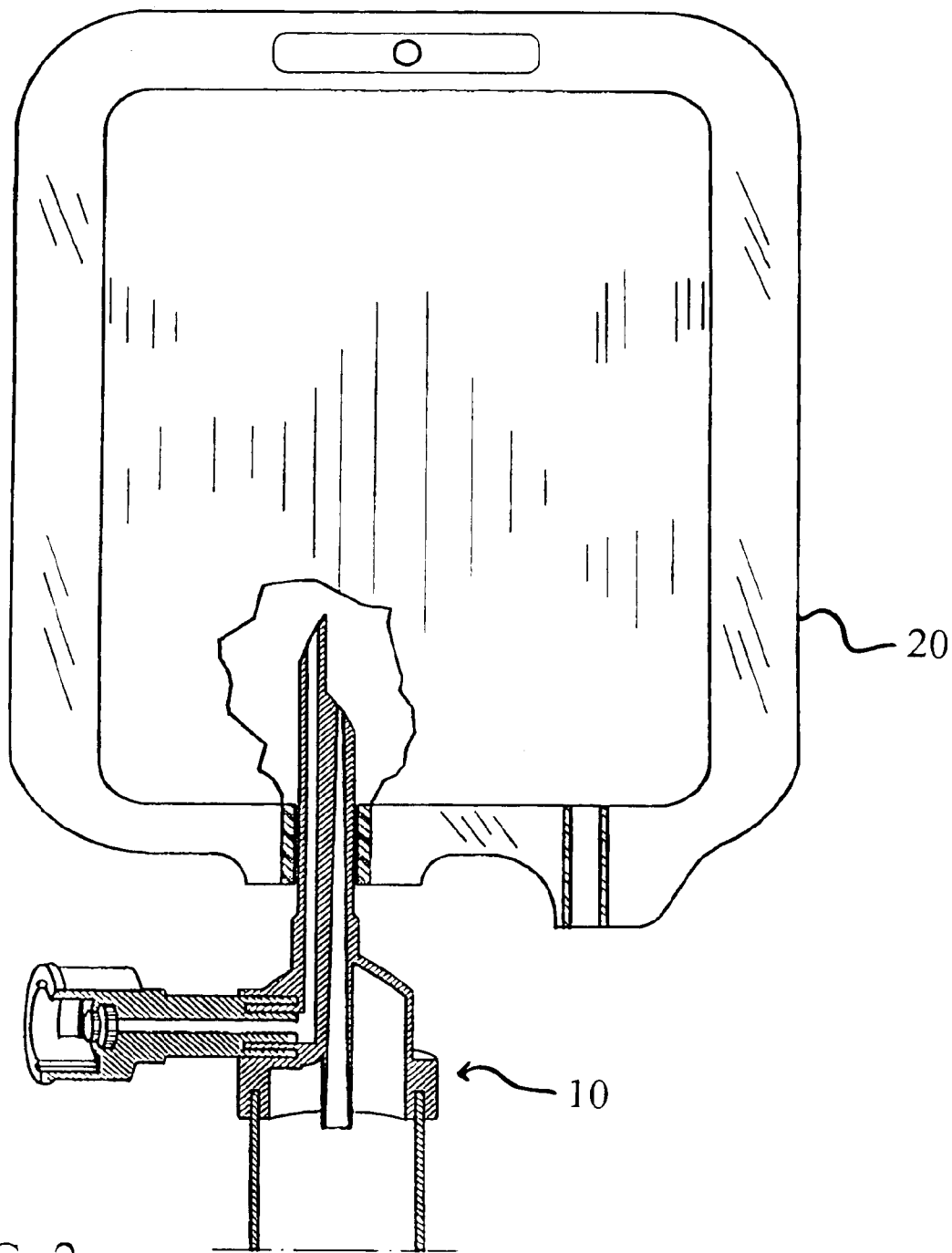
FIG. 2 is a partial cross-sectional view of the infusion device of the invention in combination with an infusion bag.

FIGS. 1 and 2 show an infusion device 10 for connecting an infusion bag 20. The infusion device comprises and insertion portion 11 for connecting the bag, and an infusion chamber 12 which in a known manner facilitates dosing a fluid flow through the chamber.

The insertion portion 11 also comprises on the one hand a flow duct 13, which extends from the bag into the chamber 12, and on the other hand a ventilating duct 14, which makes it possible to obtain a controllable supply of air to the bag so that the infusion fluid can evacuate from the bag in a controlled way. For this purpose the ventilating duct 14 is perpendicular and ends in a luer connection 15, which can be used for mounting an adjustable adjusting device for the supply of air to the bag.

A connection 16 with bayonet socket for an injector, which is not shown, is mounted outside the luer connection 15, e.g. using a cyan acrylate glue. The connection 16 is provided with a membrane 17, which is penetrable by an injection needle and which reseals when the needle is being withdrawn. A suitable material for the membrane is silicone.

When administrating via infusion with the infusion device according to the invention, the infusion device is first connected normally to a bag with an infusion fluid. The infusion chamber and the tube is thereafter filled with an infusion fluid. An injector (not shown) with a corresponding bayonet socket, which is loaded with the drug to be administrated, and with an infusion needle connected thereto is mounted in the connection 16. The needle of the injector is now used to penetrate the membrane of the injector from the injector to the bag via the ventilating duct 14. Thereafter the injector needle is withdrawn through both membranes, so that the injector can be demounted. The infusion can now be started after mixing the contents of the bag.

The invention is not limited to the above described embodiment. For instance, the above described connection 16 provided with membrane can be connected to a container of a flexible material, such as a bag, which can be used as an air container, or to receive excess fluid.

What is claimed is:

1. An infusion device lateral to the ventilation duct for administering toxic fluid comprising:

an insertion portion for connecting via a proximal end thereof to an infusion bag when in an installed condition, said insertion portion having
a flow duct connectable to said infusion bag when in an installed condition via a free, proximal outlet end of the flow duct, and
a separate ventilation duct connectable to said infusion bag when in an installed condition via a free, proximal inlet end of the ventilation duct, the insertion portion being structured to provide that both the free end of the flow duct and the free end of the ventilation duct, when in an installed condition, are in fluid contact with an interior of the infusion bag simultaneously and independently of each other, the ventilation duct and the flow duct being permanently fixed in relation to each other;
the flow duct having an outlet at an opposite, distal end thereof; and,
the ventilating duct being constructed to provide, when in the installed condition, fluid communication between the infusion bag and an exterior of said infusion device, an opposite, distal end of the ventilation duct opening to a connection arranged on a side of said infusion device for supplying said toxic fluid, wherein said connection is provided with at least one airtight, self-sealing membrane that is penetrable by an injection needle, which membrane automatically reseals upon withdrawal of the injection needle therefrom.

2. The device of claim 1, wherein the outlet of the flow duct is in fluid contact with an infusion chamber.

* * * * *